(12) United States Patent
Le Marié et al.

(10) Patent No.: US 12,144,884 B2
(45) Date of Patent: *Nov. 19, 2024

(54) SKIN BARRIER PROTECTIVE DELIVERY SYSTEMS

(71) Applicant: BOBO LABS INC., New York, NY (US)

(72) Inventors: Edouard Le Marié, Antibes (FR); Bénédicte Le Marié, Antibes (FR); Lyndon Garcines, Fountain Valley, CA (US); Adriel Carolino, Huntington Beach, CA (US); Felipe Jimenez, Rialto, CA (US); Louis C. Paul, Westport, CT (US)

(73) Assignee: BOBO LABS INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/703,772

(22) PCT Filed: Apr. 24, 2023

(86) PCT No.: PCT/US2023/019573
§ 371 (c)(1),
(2) Date: Apr. 23, 2024

(87) PCT Pub. No.: WO2023/205499
PCT Pub. Date: Oct. 26, 2023

(65) Prior Publication Data
US 2024/0325287 A1    Oct. 3, 2024

Related U.S. Application Data

(60) Provisional application No. 63/434,179, filed on Dec. 21, 2022, provisional application No. 63/333,768, filed on Apr. 22, 2022.

(51) Int. Cl.
*A61K 8/92* (2006.01)
*A61K 8/04* (2006.01)
*A61K 8/31* (2006.01)
*A61K 8/37* (2006.01)
*A61K 8/68* (2006.01)
*A61Q 17/00* (2006.01)

(52) U.S. Cl.
CPC .............. *A61K 8/922* (2013.01); *A61K 8/046* (2013.01); *A61K 8/31* (2013.01); *A61K 8/37* (2013.01); *A61K 8/68* (2013.01); *A61Q 17/00* (2013.01)

(58) Field of Classification Search
CPC . A61K 8/31; A61K 8/046; A61K 8/37; A61K 8/922; A61Q 17/00
See application file for complete search history.

(56) References Cited

U.S. PATENT DOCUMENTS

| | | |
|---|---|---|
| 10,966,914 B2 | 4/2021 | Ormancey |
| 10,996,941 B2 | 4/2021 | Krishnaswamy et al. |
| 2012/0027702 A1 | 2/2012 | Bernoud et al. |
| 2013/0310355 A1 | 11/2013 | Kulesza |
| 2017/0143610 A1 | 5/2017 | Bernoud et al. |
| 2018/0256479 A1 | 9/2018 | Bernoud et al. |
| 2019/0343753 A1 | 11/2019 | Bernoud et al. |
| 2020/0093728 A1 | 3/2020 | Lu et al. |
| 2021/0154110 A1 | 5/2021 | Bernoud |
| 2022/0087928 A1 | 3/2022 | Lerum et al. |
| 2023/0102191 A1 | 3/2023 | Wagner et al. |

OTHER PUBLICATIONS

International Search Report for Corresponding International Application No. PCT/US2023/019573, dated Aug. 21, 2023.

*Primary Examiner* — Robert A Wax
*Assistant Examiner* — Quanglong N Truong
(74) *Attorney, Agent, or Firm* — Leason Ellis LLP

(57) ABSTRACT

The present disclosure relates to compositions and methods for the treatment of topical skin conditions. Also provided are topically applied compositions and delivery systems. Also provided are methods of using the compositions and delivery systems in cosmetic, personal care and dermatology applications. Also provided is a sprayable composition that comprises petrolatum.

3 Claims, No Drawings

SKIN BARRIER PROTECTIVE DELIVERY SYSTEMS

CROSS-REFERENCE TO RELATED PATENT APPLICATIONS

This application is a U.S. National Stage Application under 35 U.S.C. § 371 of International Patent Application No. PCT/US2023/019573 filed Apr. 24, 2023, which claims the benefit of priority of U.S. Provisional Application No. 63/333,768 filed Apr. 22, 2022, both of which are incorporated by reference in their entireties. The International Application was published on Oct. 26, 2023, as International Publication No. WO/2023/205499.

1. FIELD

The present disclosure relates to topically applied products and delivery systems used in cosmetic, personal care and dermatology applications. Also provided are topically applied compositions and delivery systems. Further provided are methods of using the compositions and delivery systems in cosmetic, personal care and dermatology applications. Also provided is a composition in the form of a sprayable gel.

2. BACKGROUND

The skin is the largest organ of the body and protects mammalian organisms from both aqueous and xerotic ambient environments. It is now generally accepted that the intercellular, lamellar bilayer sheets of stratum corneum lipids are the key constituents for a functional barrier. The maintenance of a barrier against excessive transcutaneous water loss to the environment is critical to survival of all terrestrial animals. Localized or generalized perturbations of the epidermal barrier occur in a variety of diseases and conditions of the skin and mucous membrane. These perturbations not only contribute significantly to the morphology of the cutaneous lesions, but also activate certain skin diseases.

Active agents are used in skin treatments of various and diverse dermatological conditions such as psoriasis, photoaging, age spots, aged appearance of the skin due to extrinsic and intrinsic causes, skin wrinkles, acne, hyperpigmentation and skin cancers. Active agents typically are prescription active agents and non-prescription active agents. Solvents used in dermatological formulations having skin treatment active agents may be strong solvents, such as acetone, or mild, i.e., gentle, solvents. However, strong solvents are known to cause skin condition effects that require additional treatment including disruption of the skin barrier and may interfere with patients' compliance with skin treatment regimens. Mild solvents, on the other hand, are known to be ineffective in delivery of active agents in transdermal and cutaneous uses. Furthermore, with present tendency toward extended use of dermatological formulations in skincare, there is a continued need for topical formulations of active agents for various skin treatments.

Common moisturizers and emollients also cause disruptions of the barrier function. There has been and remains a need for cosmetically elegant, non-unctuous, safe and effective topical compositions that not only protects the skin barrier but also effectively and safely delivers other functional and/or pharmaceutically active ingredients to the skin.

Application of topical products by means of a user introducing a hand or inanimate applicator (brushes, spatulas, swabs, sponges, puffs) into a container can be unhygienic, and can have potentially deleterious health consequences. Even if "clean" (e.g., not containing exogenous contaminants or disease-carrying organisms), the hand can contain microorganisms present in the skin microbiome. Applicators are often not cleaned between uses and can be colonized by microorganisms.

There has been and remains a need for cosmetically elegant, non-unctuous, sprayable compositions that apply petrolatum at a safe and effective concentration of at least 30% by weight and other ingredients in a manner that not only protects the skin barrier but also effectively and safely delivers other functional and/or pharmaceutically active ingredients to the skin. Those needs are met by the skin barrier protective delivery systems of the present disclosure.

3. SUMMARY

One of the objectives of the present disclosure is to provide a cost effective composition, such as a smooth and non-sticky sprayable composition that is easy to apply and hygienic. In one embodiment, the present composition increases water retention and improves skin roughness (moisturization), repairs and protects the skin from harmful conditions.

Certain skincare formulations disclosed herein provide surprising, unexpected results. In certain embodiments, the disclosed delivery system comprises certain components that provide additive or synergistic results.

Provided in the present disclosure are compositions that are useful as skin moisturizers, skin softening agents, skin debridement agents, etc., as well as base composition for cosmetic formulations, compositions for therapeutics, e.g., pharmacological, formulations. In cosmetic formulations, the compositions can be used with added ingredients that are solely cosmetic. Alternatively, the cosmetic formulation can include ingredients that are both cosmetically efficacious and therapeutically effective, e.g., "cosmeceutical" ingredients.

In one embodiment, disclosed herein is a composition that corrects defective epidermal barrier in a skin or mucous membrane disease or condition. The compositions and methods disclosed fortify the barrier to prevent its disruption due to environmental insults. The disclosed composition is useful as moisturizers for emollition and hydration of the epidermis and produces a neutral effect on barrier function, and in certain cases improves barrier function or enhances its recovery rate.

By virtue of their effect on epidermal barrier function, the disclosed composition ameliorates epidermal hyperproliferation and diminishes inflammation. This results in significant prolonged or complete remission and prevents recurrences of skin disorders.

In certain embodiments, the skin barrier protective delivery system comprises a sprayable petrolatum that holds a higher concentration of an active ingredient without separation. It has unexpectedly been discovered that a composition comprising at least about 30% petrolatum by weight can be formulated as a spray. It has further been unexpectedly discovered that a formulation with such a high concentration of petrolatum as in the present disclosure is capable of being sprayed easily and efficiently providing even coverage on the skin. In certain embodiments, the sprayable formulation does not contain propellant gases as additives which may be harmful to the subject. In one embodiment, the composition forms an occlusive film on the skin.

In some embodiments, provided is a skin barrier protective delivery system comprised of, and preferably consisting essentially of: Coconut Alkanes and/or Coco-Caprylate/Caprate, preferably a mixture of the two, more preferably in a ratio of Coconut Alkanes to Coco-Caprylate/Caprate at from about 3:1 to about 9:1 and (b) Petrolatum at a concentration of at least about 30%; and the ratio of (a) to (b) is from about 7:3 to about 1:3. In some embodiments, the skin barrier protective delivery system is sprayable.

Optionally, the skin barrier protective delivery system of the present disclosure comprises at least one, at least two, at least three, or at least four of a ceramide, a triglyceride, a phytosterol, a phytosterol ester, a terpene (e.g., squalene), a plant-based ester or wax (e.g., jojoba esters), tocopherol and/or a phospholipid.

Optionally, the skin barrier protective delivery system of the present disclosure contains at least one, at least two, at least three, or at least four of a ceramide, a phytosterol, squalene, a plant-based ester or wax (e.g., jojoba esters), and/or a phospholipid.

In some embodiments, the skin barrier protective delivery system of the present disclosure comprises a mixture of Coconut Alkanes and Coco-Caprylate/Caprate, Petrolatum, ceramide NP, ceramide AP, jojoba esters, squalene, phytosterols, phytosteryl macadamiate, tocopherol, C18-C36 acid triglyceride, C12-18 acid triglyceride, *Ipomoea batatas* root extract, *Acacia Senegal* gum, a buffering agent (e.g., citric acid), and a sugar (e.g., maltodextrin).

In some embodiments, the skin barrier protective delivery system of the present disclosure comprises (i) at least 30 wt % Petrolatum; (ii) Coconut Alkanes in the range of 30-70 wt %; (iii) Coco-Caprylate/Caprate in the range of 3-7 wt %; (iv) ceramide NP in the range of 0.01-0.1 wt %; (v) ceramide AP in the range of 0.01-0.1 wt %; (vi) Jojoba Esters in the range of 0.1-1.5 wt %; (vii) Squalene in the range of 0.1-1 wt %; (viii) Phytosteryl Macadamiate in the range of 0.01-0.1 wt %; (ix) Phytosterols in the range of 0.005-0.1 wt %; (x) Tocopherol in the range of 0.001-0.1 wt %; (xi) C18-36 Acid Triglyceride in the range of 0.5-5 wt %; (xii) C12-18 Acid Triglyceride in the range of 0.1-1 wt %; (xiii) *Ipomoea batatas* root extract in the range of 0.01-0.1 wt %; (xiv) citric acid in the range of 0.001-0.01 wt %; (xv) *Acacia Senegal* gum in the range of 0.001-0.1 wt %; and (xvi) Maltodextrin in the range of 0.001-0.1 wt %. In some embodiments, the delivery system is a sprayable formulation. In some embodiments, the petrolatum is present at a concentration of 40 wt %. In some embodiments, the petrolatum is present at a concentration of 50 wt %.

In some embodiments, the skin barrier protective delivery system of the present disclosure comprises (i) 50 wt % Petrolatum; (ii) 42-43 wt % Coconut Alkanes; (iii) 4-5 wt % Coco-Caprylate/Caprate; (iv) 0.05 wt % ceramide NP; (v) 0.05 wt % ceramide AP; (vi) 0.75 wt % Jojoba Esters; (vii) 0.3-0.4 wt % Squalene; (viii) 0.05-0.06 wt % Phytosteryl Macadamiate; (ix) 0.01-0.02 wt % Phytosterols; (x) 0.0045 wt % Tocopherol; (xi) 1-2 wt % C18-36 Acid Triglyceride; (xii) 0.4-0.5 wt % C12-18 Acid Triglyceride; (xiii) 0.03-0.04 wt % *Ipomoea batatas* root extract; (xiv) 0.003-0.004 wt % citric acid; (xv) 0.03-0.04 wt % *Acacia Senegal* gum; and (xvi) 0.03-0.04 wt % Maltodextrin. In some embodiments, the delivery system is a sprayable formulation.

In some embodiments, the skin barrier delivery system has a viscosity of from about 500 cps to about 10,000 cps In some embodiments, provided is an emulsion comprising the skin barrier protective delivery system as described herein.

In some embodiments, the present disclosure provides a pharmaceutical composition comprising the skin barrier protective delivery system as described herein. In some embodiments, the composition is sprayable.

In some embodiments, the present disclosure provides a pharmaceutical composition in the form of a sprayable gel, comprising the skin barrier protective delivery system as described herein.

In some embodiments, the present disclosure provides a method for protecting skin of a subject in need thereof, comprising administering to the skin of the subject the skin barrier protective delivery system as described herein, or a pharmaceutical composition comprising the skin barrier protective delivery system.

In some embodiments, the present disclosure provides a method of making the skin barrier protective delivery system of any one of the preceding claims, comprising: (a) mixing petrolatum, Coconut Alkanes and Coco-Caprylate/Caprate in a reactor to create a mixture; (b) heating the mixture until a melt is obtained; and (c) cooling the mixture.

4. DETAILED DESCRIPTION

Disclosed are stable, non-irritating, skin treatment active agents containing formulations and delivery systems for topical application to the skin. The disclosed topical formulations and delivery systems provide controlled, gentle release of the active agents into the skin for the treatment of amenable skin conditions as well as for improvement of aesthetic skin properties. Also provided are methods for the formulation, manufacture and use of the disclosed formulations and delivery systems. Petrolatum is not known to have previously been utilized in non-aerosol (non-propellant based) spray formulations, meant to be dispensed via manual spray pump dispenser, as the viscosity of the petrolatum is high. Additionally, the percentage of petrolatum necessary to achieve a skin protective benefit is too high; thus, use of petrolatum can clog the spray pumps. The result would be a liquid or semi-solid (e.g., gel) composition that either does not spray at all or sprays inefficiently by sputtering through the orifice and leaving very uneven coverage on the skin. If any formulations did include petrolatum, the formulations did not include petrolatum in sufficient amounts to provide the necessary skin protectant benefits. It has now been unexpectedly discovered that a formulation with such a high concentration of petrolatum (e.g., 30% by weight or greater) as in the present disclosure is capable of being sprayed easily and efficiently providing even coverage on the skin. In certain embodiments, the sprayable formulation does not contain propellant gases as additives which can be harmful to the subject.

In certain embodiments, the formulation disclosed herein: i) allows for a reduction of use of main ingredients by a factor of 10× to 50×; ii) it is thus better for the environment; iii) the formulation leaves a silky and smooth sensation on the skin vs. a sticky, greasy and messy sensation obtained with known formulations and pure petrolatum jelly, for the same or better therapeutic effect; and iv) the formulation is a spray that provides significantly: 1) increased ease of use (at home and in hospital & nursing homes environments (e.g. one nurse vs. two) and 2) increased protection against cross bacteriological contamination (no fingers-spatula in the jar). The sprayable formulations can be applied to a skin surface without the need to touch or rub the skin surface. The risk of infection or contamination is therefore decreased. In certain embodiments, provided herein is a surprising finding of a composition comprising high percentage of petrolatum (e.g., 30% by weight or greater) in a sprayable form with improved sprayability compared to existing compositions comprising petrolatum.

In some embodiments, provided is a skin barrier protective delivery system comprising Coconut Alkanes and/or Coco-Caprylate/Caprate, preferably a mixture of the two, more preferably in a ratio of Coconut Alkanes to Coco-Caprylate/Caprate at from about 3:1 to about 9:1 and (b) Petrolatum at a concentration of at least about 30%; and the ratio of (a) to (b) is from about 7:3 to about 1:3. In some embodiments, the skin barrier protective delivery system is sprayable.

In some embodiments, provided is a skin barrier protective delivery system consisting essentially of Coconut Alkanes and/or Coco-Caprylate/Caprate, preferably a mixture of the two, more preferably in a ratio of Coconut Alkanes to Coco-Caprylate/Caprate at from about 3:1 to about 9:1 and (b) Petrolatum at a concentration of at least about 30%; and the ratio of (a) to (b) is from about 7:3 to about 1:3. In some embodiments, the skin barrier protective delivery system is sprayable.

In some embodiments of the skin barrier protective delivery system of the present disclosure, the ratio of (a) Coconut Alkanes and/or Coco-Caprylate/Caprate, preferably a mixture of the two, to (b) Petrolatum is from about 2:1 to about 1:2.

In other embodiments of the skin barrier protective delivery system of the present disclosure, the ratio of (a) Coconut Alkanes and/or Coco-Caprylate/Caprate, preferably a mixture of the two, to (b) Petrolatum is from about 3:2 to about 2:3.

In still other embodiments of the skin barrier protective delivery system of the present disclosure, the ratio of (a) Coconut Alkanes and/or Coco-Caprylate/Caprate, preferably a mixture of the two, to (b) Petrolatum is from about 5:4 to about 4:5, and even more preferably is about 10:9 to about 9:10, and most preferably about 1:1.

In these embodiments, that ratio of (i) Coconut Alkanes to (ii) Coco-Caprylate/Caprate is from about 3:1 to about 9:1.

Petrolatum

Petrolatum is a combination of hydrocarbons obtained as a semi-solid from dewaxing paraffinic residual oil. It consists predominantly of saturated crystalline and liquid hydrocarbons, predominately having a carbon chain length of $C_{25}$ and above.

Petrolatum has a long history as a safe and effective topical agent suitable for use in a wide range of topical applications including, but not limited to: moisturizing creams and lotions; make-up; hand and foot creams and lotions; skin protectants; wound care; lip balms and lipsticks; salves and rubs; baby care; hair care. In pharmaceuticals, petrolatum is a commonly used based for medicated pain balms, ointments, and creams.

In 1983, the U.S. Food and Drug Administration approved petrolatum for inclusion in its Final Monograph for Skin Protectant Drug Products for Over-the-Counter Human Use. In the public comments published as part of the rulemaking process, FDA included the following rationale: "The use of petrolatum as an emollient has been well accepted for dry skin conditions, especially with flaking skin such as sunburn, and chapping." 43 Federal Register (Fed. Reg.) 34628 at 34639. The FDA assessment of the safety and efficacy of petrolatum in topical application was further justified: "Petrolatum is not absorbed through intact or injured skin and is neither sensitizing nor irritating. . . . Clinical and marketing experience has confirmed that petrolatum is safe in the OTC dosage range used as a skin protectant." 43 Fed. Reg. at 33372.

Under U.S. law, cosmetic, personal care and dermatologic products that contain more than 30% petrolatum may make skin protectant "label" claims-namely, that the product temporarily protects injured or exposed skin or mucous membrane surfaces from harmful or annoying stimuli and may help provide relief to such surfaces. More particularly, such products may claim as benefits: helping to prevent (or temporarily protecting; and, optionally, helping to relieve) chafed, chapped, or cracked skin.

Lip products that contain petrolatum at a concentration recognized to be safe and effective by the FDA in its final Skin Protectant Monograph may claim, as a benefit, temporarily preventing dryness and helping to relieve chapping of the exposed surfaces of the lips.

Both skin and lip products that contain over 30% petrolatum may also claim helping to protect the skin/lips from the drying effects of wind and cold weather.

Despite its long history of safety and efficacy, petrolatum-based topical formulations are known to have certain limitations-they can be unctuous and cosmetically-inelegant.

Coconut Alkanes and Coco-Caprylate/Caprate

Coconut Alkanes are produced by reduction and hydrogenation of a mixture of fatty acids derived from Coconut Oil. Different carbon chain lengths and the distributions of different carbon chain lengths are commercially available, including from Biosynthesis Ltd. (Saint-Cyr-sous-Dourdan France), ranging from $C_5$-$C_{14}$, including $C_8$-$C_{10}$, $C_9$-$C_{12}$ and $C_{12}$-$C_{14}$, and mixtures of the foregoing. Coconut Alkanes are described in US Pre-Grant Patent Application Publication Nos. 2012/0027702, 2017/0143610, 2018/0256479, 2019/0343753, 2019/0343753, and 2021/0154110 the disclosures of each of which are incorporated in pertinent part in their entireties.

Coco-Caprylate/Caprate (CAS #95912-86-0) is a mixture of esters of Coconut Alcohol (mixture of fatty alcohols derived from Coconut Oil) with Caprylic Acid and Capric Acid. Non-limiting examples of commercially available Coco-Caprylate/Caprate include Cetiol® LC (BASF Corporation, Florham Park, NJ), Dub 810 C (Stearinerie Dubois Fils, Boulogne Billancourt, France), and Lanol™ 2681 (Seppic, Paris, France).

A mixture of Coconut Alkanes and Coco-Caprylate/Caprate is commercially available from manufacturers of specialty raw materials (and their distributors), including under the tradenames Vegelight® 1214 (from Biosynthesis) and Vesgesil™ 345 (Global Ingredient Solutions, Irvine, CA). The ratio of Coconut Alkanes to Coco-Caprylate/Caprate can vary.

Other Excipients

In some embodiments, skin barrier protective delivery systems of the present disclosure further comprise at least one of a ceramide, a triglyceride, a phytosterol, a phytosterol ester, a terpene (e.g., squalene), a plant-based ester or wax, tocopherol and/or a phospholipid. In some embodiments, skin barrier protective delivery systems of the present disclosure comprise at least two of a ceramide, a triglyceride, a phytosterol, a phytosterol ester, a terpene, a plant-based ester or wax, tocopherol and/or a phospholipid. In some embodiments, skin barrier protective delivery systems of the present disclosure comprise at least three of a ceramide, a triglyceride, a phytosterol, a phytosterol ester, a terpene, a plant-based ester or wax, tocopherol and/or a phospholipid. In some embodiments, skin barrier protective delivery systems of the present disclosure comprise at least four of a ceramide, a triglyceride, a phytosterol, a phytosterol ester, a terpene, a plant-based ester or wax, tocopherol and/or a phospholipid. In some embodiments, skin barrier protective delivery systems of the present disclosure comprise a ceramide, a triglyceride, a phytosterol, a phytosterol ester, a terpene, a plant-based ester or wax, tocopherol and/or a phospholipid.

In some embodiments, skin barrier protective delivery systems of the present disclosure comprise a plant-based ester or wax. Plant oils, plant-derived esters and waxes, sterols, and esters of phytosterols and fatty acids (e.g., derived from plant seed oils) can be used in cosmetic, personal care and dermatology products.

Plant oils, plant-derived esters and waxes, sterols, and esters of phytosterols and fatty acids (e.g., derived from plant seed oils) are widely used in cosmetic, personal care and dermatology products. In some embodiments, the plant-based oil, ester or wax comprises a jojoba ester.

*Simmondsia Chinensis* (Jojoba) Seed Oil is the fixed oil expressed or extracted from seeds of the desert shrub, Jojoba, *Simmondsia chinensis*.

Macadamia Integrifolia Seed Oil is the fixed oil obtained from the nut of Macadamia integrifolia.

Jojoba Oil/Macadamia Seed Oil Esters (CAS #97593-46-9) is a mixture of esters formed by the transesterification of Jojoba Seed Oil and Macadamia integrifolia Seed Oil. In some embodiments, the skin barrier protective delivery system of the present disclosure comprises at least one ceramide, preferably at least two ceramides. Ceramides are a group of sphingolipids containing derivatives of sphingosine bases in amide linkage with a variety of fatty acids. Together with other stratum corneum lipids, ceramides play an essential role in structuring and maintaining the barrier function of the skin. The at least one ceramide, when present, is included in the skin barrier protective delivery system of the present disclosure is preferably at a concentration ranging from about 0.05% to about 0.5%.

Preferably, the ceramides are one or both of Ceramide AP and/or Ceramide NP. Ceramide AP is an N-acylated sphingolipid consisting of phytosphingosine having a D-erythro structure linked to an alpha-hydroxy saturated or unsaturated fatty acid. Ceramide NP is an N-acylated sphingolipid consisting of phytosphingosine having a D-erythro structure linked to normal saturated or unsaturated fatty acid.

Many dermatological conditions and disorders that have a diminished skin barrier function are characterized by a decrease in ceramide content. Topical formulations that deliver lipids identical to, or that mimic, those in skin are reported to improve skin conditions. See, e.g., Coderch, L., López, O., de la Maza A., Parra J. "Ceramides and skin function" Am. J. Clin. Dermatol. 2003; 4 (2): 107-29.

In some embodiments, the skin barrier protective delivery system of the present disclosure comprises at least one phytosterol. Phytosterols ($C_{17}H_{28}O$; CAS #949109-75-5) are a family of plant-derived alcohols of gonanes, a tetracyclic hydrocarbon with no double bonds. More specifically, the hydrogen atom in position 3 of the gonane is replaced by a hydroxyl group.

In some embodiments, the skin barrier protective delivery system of the present disclosure comprises at least one terpene. In some embodiments, the terpene is squalene. Squalene (CAS #111-02-4) is an unsaturated branched chain isoprenoid hydrocarbon found in a variety of plant oils or derived through fermentation. Squalene, when present, is preferably included in the skin barrier protective delivery system of the present disclosure at a concentration of up 5%, for example less than about 2%, at a concentration of less than about 1%, or at a concentration of less than about 0.5%.

In some embodiments, the skin barrier protective delivery system comprises Vitamin E or any of its forms, for example tocopherol. Vitamin E is a plant-derived, lipid-soluble substance comprised of a chromanol ring with a side chain located at the $C_2$ position. Tocopherol (CAS #10191-41-0) are forms of Vitamin E—designated alpha, beta, gamma, and delta, based on the number and position of methyl groups on the chromanol ring. Some embodiments of the skin barrier protective delivery system of the present disclosure comprise at least one ceramide, at least two ceramides, at least one phytosterol and/or squalene.

Some embodiments of the skin barrier protective delivery system of the present disclosure comprise at least one ceramide, at least two ceramides, at least one phytosterol and squalene.

Each of the above embodiments may contain one or a mixture of plant-derived esters.

Exemplary plant-derived esters include Jojoba Oil/Macadamia Seed Oil Esters and/or Phytosteryl Macadamiate. Phytosteryl Macadamiate (CAS #68990-51-2) is the ester of phytosterol and the fatty acids from Macadamia Integrifolia Seed Oil.

In some embodiments, the skin barrier protective delivery system of the present disclosure comprises Jojoba Oil/Macadamia Seed Oil Esters and Phytosteryl Macadamiate.

Plant-based esters, when present, are included in the skin barrier protective delivery system of the present disclosure alone, or in combination with one or more plant oils or waxes, at a combined concentration of up to about 20%, preferably up to about 15%, still more preferably up to about 10%, and even more preferably up to about 5%.

A variety of functional ingredients, including natural, plant- and algal-derived ingredients, as well as active pharmaceutical ingredients, can be incorporated in the skin barrier protective delivery systems of the present disclosure.

Skin lipid content-notably, triglycerides, wax esters, squalene, phospholipids, sterols and sterol esters—can and does vary by age. Cotterill, J. A., W. J. Cunliffe, B. Williamson, and L. Bulusu. "Age and Sex Variation in Skin Surface Lipid Composition and Sebum Excretion Rate." Br. J. Dermatol. (1972); 87:333-40.

Designed to mimic the distribution of skin lipids in "younger skin," L22® (Flora Technologies, Ltd., Chandler, AZ) is comprised of Jojoba Oil/Macadamia Seed Oil Esters, Squalene, Phytosteryl Macadamiate, Phytosterols and Tocopherol. The primary components of L22 are Jojoba Oil/Macadamia Seed Oil Esters (approx. 85%) and Squalene (12.5%). Phytosteryl Macadamiate and Phytosterols are present in L22 at a combined concentration of about 2.5%.

"Active ingredients" may be incorporated (i.e., included) in the skin barrier protective delivery system of the present disclosure at a concentration ranging from about 0.001% to about 20% preferably from about 0.005% to about 10% by weight, more preferably from about 0.01% to about 5% by weight, and even more preferably from about 0.1% to about 2.0%, and include: agents for the =treatment of inflammatory dermatosis (including acne, eczema, psoriasis, rosacea, and from radiation exposure), both steroidal and non-steroidal; anti-microbial and anti-fungal actives; anti-itch agents; topical anaesthetics; sunscreens; emollients and skin soothing agents; humectants and moisturizing agents, including hyaluronic acid; skin barrier protectants (as defined in the U.S. FDA OTC Final Monograph); lipids, including vegetal-derived oils and butters; antioxidants and agents that reduce the appearance of fine lines and wrinkles, including vitamins, proteins and peptides; skin bleaching and lightening agents; agents that contribute to wound healing/wound cosmesis; agents that reduce inflammation (including erythema) and/or edema; active pharmaceutical ingredients (over-the-counter or prescription) that prevent or treat (or help prevent or treat) a pathophysiological condition (e.g., disease), including but not limited to ulcerated skin.

One non-limiting "active" ingredient that is included in the skin barrier protective delivery system of the present disclosure is *Ipomoea batatas* Root Extract, which when applied in accordance with the present disclosure has been shown to reduce edema in extremities.

A novel and basic characteristic of embodiments of the present disclosure that are directed to skin barrier protective delivery system consisting essentially of: (a) Coconut Alkanes and/or Coco-Caprylate/Caprate, preferably a mixture of the two, more preferably in a ratio of Coconut Alkanes to Coco-Caprylate/Caprate at from about 3:1 to about 9:1 and (b) Petrolatum at a concentration of at least about 30%; and the ratio of (a) to (b) is from about 7:3 to about 1:3, is that the skin barrier protective delivery system is sprayable.

The skin barrier protective delivery system of the present disclosure is preferably applied by spraying or misting, and preferably has a viscosity (TE@ 10) of from about 500 cps to 10,000 cps. Devices that may be used for spraying or misting are known to the person having ordinary skill in the art and include pump sprays, trigger sprays, atomizers, aerosol containers (pressurized with a propellant, preferably a non-fluorocarbon propellant, including bag-on-valve dispensers.)

Numbers used in describing quantities of ingredients are to be understood as being modified in all instances by the term "about."

Unless otherwise indicated, percentages are to be understood as based upon the total weight of the skin barrier protective delivery system.

Numerical ranges are meant to include numbers within the recited range, and combinations of subranges between, the given ranges. For example, a range from 1-5, includes 1, 2, 3, 4 and 5, as well as subranges such as 2-5, 3-5, 2-3, 2-4, 1-4, etc.

"At least one" means one or more, and also includes individual components as well as mixtures/combinations.

The following examples are illustrative. Modifications will be apparent to, and can be readily made by, those skilled in the art without departing from the spirit and scope of the disclosure. The scope of the appended claims is not to be limited to the examples.

5. EXAMPLES

Example 1-Skin Protectant Spray

| INCI Name | Wt % | Wt % | Wt % |
| --- | --- | --- | --- |
| Snow White Petrolatum USP | 30.0 | 65.0 | 50.0 |
| Coconut Alkanes and Coco-Caprylate/Caprate | 65.0 | 30.0 | 45.0-47.5 |
| Ceramide(s) | 0.05-0.5 | 0.05-0.5 | 0.05-0.5 |
| Jojoba Oil/Macadamia Seed Oil Esters | <5.0 | <5.0 | 2.5 |
| Squalene | <2.0 | <1.0 | <0.5 |
| Phytosteryl Macadamiate | 0.01-0.1 | 0.01-0.1 | 0.01-0.1 |
| Phytosterol | 0.05-0.3 | 0.05-0.3 | <0.2 |
| Tocopherol | 0.01-0.25 | 0.01-0.25 | <0.05 |
| Ipomoea Batatas Root Extract | 0.01-5 | 0.01-5 | <0.1 |

Example 2-Skin Protectant Spray

| Ingredients/Range of Wt % and specific example | Minimum Wt % | Specific Wt % | Max. Wt % |
| --- | --- | --- | --- |
| Petrolatum up to 60% | 30 | 50 | 60 |
| Coconut Alkanes | 30 | 45 | 70 |
| Coco-Caprylate/Caprate | 3 | 5 | 10 |
| C 18-36 Acid Triglyceride | 0.5 | 2 | 5 |
| Ipomoea Batatas Root Extract | 0.01 | 0.05 | 0.1 |
| Jojoba Oil/Macadamia Seed Oil Esters | 0.1 | 0.75 | 1.5 |
| Ceramide AP | 0.01 | 0.05 | 0.1 |
| Ceramide NP | 0.01 | 0.05 | 0.1 |
| Squalene | 0.1 | 0.37 | 1 |
| Tocopherol | 0.001 | 0.0045 | 0.1 |
| Phytosterols | 0.005 | 0.02 | 0.1 |
| C 12-18 Acid Triglyceride | 0.1 | 0.5 | 1 |
| Phytosteryl Macadamiate | 0.01 | 0.07 | 0.1 |
| Acacia Senegal Gum | 0.01 | 0.04 | 0.1 |
| Citric Acid | 0.001 | 0.003 | 0.01 |

INITIAL SPECIFICATIONS:

Appearance: Hazy, semi-viscous liquid
Color: Purple
Odor: Characteristic
pH: N/A
Viscosity (Brookfield DV-11+:
Spindle T-E @ 10 rpm,
25° C. J: 3,500 cps

Example 3-Skin Protectant Spray

| INCI Name/Range of wt % | Minimum wt % | Specific wt % | Max wt % |
| --- | --- | --- | --- |
| Petrolatum USP | 30.0 | 50.0 | 70.0 |
| Coconut Alkanes and Coco-Caprylate/Caprate | 30.0 | 46.0 | 70 |
| C18-36 Acid Triglyceride | 0.5 | 1.5 | 5 |
| Ceramide(s) | 0.02 | 0.1 | 0.5 |
| Jojoba Oil/Macadamia Seed Oil Esters | 0.1 | 1 | 2.5 |
| Squalene | 0.1 | 0.5 | 1 |
| Phytosteryl Macadamiate | 0.01 | 0.06 | 0.1 |
| Phytosterol | 0.05 | 0.15 | 0.2 |
| Tocopherol | 0.01 | 0.0045 | 0.25 |
| Ipomoea Batatas Root Extract | 0.01 | 0.05 | 5 |
| C12-18 Acid Triglyceride | 0.1 | 0.5 | 1 |
| Acacia Senegal Gum | 0.001 | 0.02 | 0.1 |
| Maltodextrin | 0.001 | 0.03 | 0.1 |
| Citric Acid | 0.001 | 0.03 | 0.1 |

Example 4-Skin Protectant Spray

| Ingredients/Range of wt % | Minimum wt % | Specific wt % | Max wt % |
| --- | --- | --- | --- |
| Petrolatum (Snow White petrolatum USP) | 30 | 50 | 70 |

-continued

| Ingredients/Range of wt % | Minimum wt % | Specific wt % | Max wt % |
|---|---|---|---|
| Coconut Alkanes | 30 | 42.12 | 70 |
| Coco-Caprylate/Caprate | 3 | 4.68 | 7 |
| C18-36 Acid Triglyceride | 0.5 | 1.38 | 5 |
| C12-18 Acid Triglyceride | 0.1 | 0.42 | 1 |
| Ceramide NP | 0.01 | 0.05 | 0.1 |
| Ceramide AP | 0.01 | 0.05 | 0.1 |
| Jojoba Esters | 0.1 | 0.75 | 1.5 |
| Squalene | 0.1 | 0.37 | 1 |
| Phytosteryl Macadamiate | 0.01 | 0.063 | 0.1 |
| Phytosterols | 0.005 | 0.15 | 0.1 |
| Tocopherol | 0.001 | 0.0045 | 0.1 |
| Ipomoea Batatas Root Extract | 0.01 | 0.033 | 0.1 |
| Citric Acid | 0.001 | 0.003 | 0.01 |
| Acacia Senegal Gum | 0.001 | 0.033 | 0.1 |
| Maltodextrin | 0.001 | 0.031 | 0.1 |

Example 5-Skin Protectant Spray

| Ingredients: | % wt/wt | % Breakdown | INCI name |
|---|---|---|---|
| Snow White petrolatum USP | 50.0 | 100.0 | Petrolatum |
| Vegesil 345 | 46.8 | 90.0 | (i) Coconut Alkanes |
|  |  | 10.0 | (ii) Coco-Caprylate/Caprate |
| Ceramide IIIB | 0.05 | 100.0 | Ceramide NP |
| Ceramide VI | 0.05 | 100.0 | Ceramide AP |
| L22 | 3.0 | 25.0 | (i) Jojoba Esters |
|  |  | 12.25 | (ii) Squalene |
|  |  | 2.1 | (iii) Phytosteryl Macadamiate |
|  |  | 0.5 | (iv) Phytosterols |
|  |  | 0.15 | (v) Tocopherol |
|  |  | 46.0 | (vi) C18-36 Acid Triglyceride |
|  |  | 14.0 | (vii) C12-18 Acid Triglyceride |
| Natpure Xfine Potato SP313 | 0.1 |  |  |
|  |  | 33.0 | (i) Ipomoea Batatas Root Extract |
|  |  |  | (ii) Citric Acid |
|  |  | 3.0 | (iii) Acacia Senegal Gum |
|  |  | 33.0 |  |
|  |  | 31.0 | (iv) Maltodextrin |

| Physical Properties: | Specification limits: |
|---|---|
| Appearance: | Translucent, slightly viscous gel |
| Color: | Purple |
| Odor: | Characteristic |
| Specific Gravity @ 25° C. | 0.78-0.83 |
| Viscosity @ 25° C. (Brookfield DVII+: Spindle RV-4 @ 10 rpm, 1 min) | 1,000 cps-5,000 cps |
| Supplementary Tests Petrolatum in the range of 40.0%-60.0% |  |
| Microbiological Tests Aerobic plate count | Less than 10 CFU/g |
| Yeast and mold | Less than 10 CFU/g |

Example 6-Skin Protectant Spray

| INCI Name/Specific Wt % | Minimum wt % | Specific wt % | Max. wt % |
|---|---|---|---|
| Snow White Petrolatum USP | 30.0 | 65.0 | 50.0 |
| Coconut Alkanes and Coco-Caprylate/Caprate | 65.0 | 30.0 | 45.0-47.5 |
| Ceramide(s) | 0.05-0.5 | 0.05-0.5 | 0.05-0.5 |
| Jojoba Oil/Macadamia Seed Oil Esters | <5.0 | <5.0 | 2.5 |
| Squalene | <2.0 | <1.0 | <0.5 |
| Phytosteryl Macadamiate | 0.01-0.1 | 0.01-0.1 | 0.01-0.1 |
| Phytosterol | 0.05-0.3 | 0.05-0.3 | <0.2 |
| Tocopherol | 0.01-0.25 | 0.01-0.25 | <0.05 |
| Ipomoea Batatas Root Extract | 0.01-5 | 0.01-5 | <0.1 |

Example 7-Skin Protectant Spray

| INCI Name/Range of wt % and specific example | Minimum Wt % | Specific Wt % | Max Wt % |
|---|---|---|---|
| Snow White Petrolatum USP | 30 | 50.0 | 70 |
| Coconut Alkanes and Coco-Caprylate/Caprate | 30 | 47.5 | 65 |
| Ceramide(s) | 0.05 | 0.25 | 0.5 |
| Jojoba Oil/Macadamia Seed Oil Esters | 0.1 | 0.75 | 1.5 |
| Squalene | 0.1 | 0.37 | 1 |
| Phytosteryl Macadamiate | 0.01 | 0.063 | 0.1 |
| Phytosterol | 0.005 | 0.015 | 0.1 |
| Tocopherol | 0.001 | 0.0045 | 0.1 |
| Ipomoea Batatas Root Extract | 0.01 | 0.033 | 0.1 |

Example 8-Method of Making the Formulation

Individual ingredients were weighed and measured and placed in separate, clean, properly identified suitable size tared containers.

Step 1: Snow White Petrolatum USP was added into a main reactor vessel that was equipped with a propeller mixer. The power and temperature of the main reactor vessel were controlled with variable speed controls. The Snow White Petrolatum USP was mixed under high speed and heat to 50° C.-55° C. and maintained at this temperature.

Step 2: In a separate vessel, Vegesil and ceramides were mixed and heated to 85° C.-90° C. until uniform. After the Vegesil and ceramides are melted and well combined, the mixture was then slowly added to the main reactor vessel in step 1 and mixed until uniform. The temperature was maintained at 50° C.-55° C.

Step 3: In a separate vessel, L22 and Natpure Xfine Potato were mixed until uniform and maintained at 50° C.-55° C. The mixture was then slowly added to the main reactor vessel of step 1 and mixed until uniform. The mixture in the main reactor vessel was then removed from the heat and homogenized until the Natpure Xfine Potato SP313 was uniformly dispersed.

Step 4: Continue mixing the mixture in the main reactor vessel and cooling the mixture to 35° C. A sample of the mixture was then tested and approved.

Exemplary Products, Systems and Methods are Set Out in the Following Items:

1. A skin barrier protective delivery system comprised of:
   (a) a mixture of Coconut Alkanes and Coco-Caprylate/Caprate and (b) Petrolatum, wherein petrolatum is present at a concentration of at least 30%, and the ratio of (a) to (b) is from 7:3 to 1:3.

2. A skin barrier protective delivery system consisting essentially of: (a) a mixture of Coconut Alkanes and Coco-Caprylate/Caprate and (b) Petrolatum, wherein petrolatum is present at a concentration of at least 30%, and the ratio of (a) to (b) is from 7:3 to 1:3.
3. The skin barrier protective delivery system of item 1 or 2, wherein the ratio of Coconut Alkanes to Coco-Caprylate/Caprate is from about from about 7:3 to about 1:3.
4. The skin barrier protective delivery system of any one of items 1-3, further comprising at least one of a ceramide, a triglyceride, a phytosterol, a phytosterol ester, a terpene, a plant-based ester or wax, tocopherol and/or a phospholipid.
5. The skin barrier protective delivery system of any of items 1-4, further containing at least one of a ceramide, a phytosterol, squalene, a plant-based esters or wax, and/or a phospholipid.
6. The skin barrier protective delivery system of any of items 1-4, further containing at least two of a ceramide, a phytosterol, squalene, a plant-based esters or wax, and/or a phospholipid.
7. An emulsion comprising the skin barrier protective delivery system of any of items 1-6.
8. The skin barrier protective delivery system of any of items 1-7, that is sprayable.
9. The skin barrier protective delivery system of any one of items 1-8, having a viscosity of from about 500 cps to about 10,000 cps.
10. A skin barrier protective delivery system comprising a mixture of Coconut Alkanes and Coco-Caprylate/Caprate, Petrolatum, ceramide NP, ceramide AP, jojoba esters, squalene, phytosterols, phytosteryl macadamiate, tocopherol, C18-C36 acid triglyceride, C12-18 acid triglyceride, *Ipomoea batatas* root extract, *Acacia Senegal* gum, citric acid, and maltodextrin.
11. A skin barrier protective delivery system comprising
    (i) at least 30 wt % Petrolatum;
    (ii) Coconut Alkanes in the range of 30-70 wt %;
    (iii) Coco-Caprylate/Caprate in the range of 3-7 wt %;
    (iv) ceramide NP in the range of 0.01-0.1 wt %;
    (v) ceramide AP in the range of 0.01-0.1 wt %;
    (vi) Jojoba Esters in the range of 0.1-1.5 wt %;
    (vii) Squalene in the range of 0.1-1 wt %;
    (viii) Phytosteryl Macadamiate in the range of 0.01-0.1 wt %;
    (ix) Phytosterols in the range of 0.005-0.1 wt %;
    (x) Tocopherol in the range of 0.001-0.1 wt %;
    (xi) C18-36 Acid Triglyceride in the range of 0.5-5 wt %;
    (xii) C12-18 Acid Triglyceride in the range of 0.1-1 wt %;
    (xiii) *Ipomoea batatas* root extract in the range of 0.01-0.1 wt %;
    (xiv) citric acid in the range of 0.001-0.01 wt %;
    (xv) *Acacia Senegal* gum in the range of 0.001-0.1 wt %; and
    (xvi) Maltodextrin in the range of 0.001-0.1 wt %,
    wherein the delivery system is a sprayable formulation.
12. The skin barrier protective delivery system of item 9, comprising:
    (i) 50 wt % Petrolatum;
    (ii) 42-43 wt % Coconut Alkanes;
    (iii) 4-5 wt % Coco-Caprylate/Caprate;
    (iv) 0.05 wt % ceramide NP;
    (v) 0.05 wt % ceramide AP;
    (vi) 0.75 wt % Jojoba Esters;
    (vii) 0.3-0.4 wt % Squalene;
    (viii) 0.05-0.06 wt % Phytosteryl Macadamiate;
    (ix) 0.01-0.02 wt % Phytosterols;
    (x) 0.0045 wt % Tocopherol;
    (xi) 1-2 wt % C18-36 Acid Triglyceride;
    (xii) 0.4-0.5 wt % C12-18 Acid Triglyceride;
    (xiii) 0.03-0.04 wt % *Ipomoea batatas* root extract;
    (xiv) 0.003-0.004 wt % citric acid;
    (xv) 0.03-0.04 wt % *Acacia Senegal* gum; and
    (xvi) 0.03-0.04 wt % Maltodextrin.
13. A pharmaceutical composition comprising the skin barrier protective delivery system of any one of the preceding items.
14. A pharmaceutical composition in the form of a sprayable gel, comprising the skin barrier protective delivery system of any one of the preceding items.
15. A method for protecting skin of a subject in need thereof, comprising administering to the skin of the subject the skin barrier protective delivery system of any one of items 1-12, a pharmaceutical composition according to item 13 or 14.
16. A method of making the skin barrier protective delivery system of any one of the preceding items, comprising: (a) mixing petrolatum, Coconut Alkanes and Coco-Caprylate/Caprate in a reactor to create a mixture; (b) heating the mixture until a melt is obtained; and (c) cooling the mixture.

The invention claimed is:
1. A skin barrier protective delivery system comprising a mixture of each of the following components: Coconut Alkanes and Coco-Caprylate/Caprate, Petrolatum, ceramide NP, ceramide AP, jojoba esters, squalene, phytosterols, phytosteryl macadamiate, tocopherol, C18-C36 acid triglyceride, C12-18 acid triglyceride, *Ipomoea batatas* root extract, *Acacia senegal* gum, citric acid, and maltodextrin, wherein the C18-C36 acid triglyceride is different from the C12-18 acid triglyceride.
2. A skin barrier protective delivery system comprises each of the following components:
    (i) at least 30 wt % Petrolatum;
    (ii) Coconut Alkanes in the range of 30-70 wt %;
    (iii) Coco-Caprylate/Caprate in the range of 3-7 wt %;
    (iv) ceramide NP in the range of 0.01-0.1 wt %;
    (v) ceramide AP in the range of 0.01-0.1 wt %;
    (vi) Jojoba Esters in the range of 0.1-1.5 wt %;
    (vii) Squalene in the range of 0.1-1 wt %;
    (viii) Phytosteryl Macadamiate in the range of 0.01-0.1 wt %;
    (ix) Phytosterols in the range of 0.005-0.1 wt %;
    (x) Tocopherol in the range of 0.001-0.1 wt %;
    (xi) C18-36 Acid Triglyceride in the range of 0.5-5 wt %;
    (xii) C12-18 Acid Triglyceride in the range of 0.1-1 wt %;
    (xiii) *Ipomoea Batatas* root extract in the range of 0.01-0.1 wt %;
    (xiv) citric acid in the range of 0.001-0.01 wt %;
    (xv) *Acacia senegal* gum in the range of 0.001-0.1 wt %; and
    (xvi) Maltodextrin in the range of 0.001-0.1 wt %,
    wherein the delivery system is a sprayable formulation, and wherein the C18-C36 acid triglyceride is different from the C12-18 acid triglyceride.
3. A skin barrier protective delivery system comprised of: (a) a mixture of Coconut Alkanes and Coco-Caprylate/Caprate and (b) Petrolatum, wherein petrolatum is present at a concentration of at least 30%, and the ratio of (a) to (b) is from 7:3 to 1:3, wherein said skin barrier protective delivery system having a viscosity of from about 500 cps to about

10,000 cps, wherein said skin barrier protective delivery system comprises each of the following components:
- (i) 50 wt % Petrolatum;
- (ii) 42-43 wt % Coconut Alkanes;
- (iii) 4-5 wt % Coco-Caprylate/Caprate;
- (iv) 0.05 wt % ceramide NP;
- (v) 0.05 wt % ceramide AP;
- (vi) 0.75 wt % Jojoba Esters;
- (vii) 0.3-0.4 wt % Squalene;
- (viii) 0.05-0.06 wt % Phytosteryl Macadamiate;
- (ix) 0.01-0.02 wt % Phytosterols;
- (x) 0.0045 wt % Tocopherol;
- (xi) 1-2 wt % C18-36 Acid Triglyceride;
- (xii) 0.4-0.5 wt % C12-18 Acid Triglyceride;
- (xiii) 0.03-0.04 wt % *Ipomoea batatas* root extract;
- (xiv) 0.003-0.004 wt % citric acid;
- (xv) 0.03-0.04 wt % *Acacia senegal* gum; and
- (xvi) 0.03-0.04 wt % Maltodextrin, wherein the C18-C36 acid triglyceride is different from the C12-18 acid triglyceride.

* * * * *